United States Patent [19]
Gelland et al.

[11] Patent Number: 5,658,881
[45] Date of Patent: Aug. 19, 1997

[54] METHOD FOR TOPICAL INHIBITION OF THE METABOLIC ACTIVITY OF CYTOCHROME P450

[75] Inventors: Yuri Gelland, Pittsburgh, Pa.; Bruce L. Wolf, Nashville, Tenn.

[73] Assignee: TWK, Inc., Nashville, Tenn.

[21] Appl. No.: 323,267

[22] Filed: Oct. 14, 1994

[51] Int. Cl.⁶ .................. A61K 31/57; A61K 31/415; A61K 31/495; A61K 38/13
[52] U.S. Cl. .................. 514/11; 514/171; 514/252; 514/399
[58] Field of Search .................. 514/171, 252, 514/399, 11

[56] References Cited

U.S. PATENT DOCUMENTS

| | | | |
|---|---|---|---|
| 4,089,959 | 5/1978 | Diamond | 424/253 |
| 5,081,114 | 1/1992 | Gourvest et al. | 514/177 |
| 5,215,965 | 6/1993 | Lezdey et al. | 514/12 |

OTHER PUBLICATIONS

M. Harman, L. Hendeles, Clinical Relevance of the Interaction of Theophylline with Diltiazen or Nifedipine, Feb., 1989.

D. Sesardic, et al., Furafylline is a Potent and Selective Inhibitor of Cytochrome P–450 1A2 in Man, Jun., 1990.

T. Iwana, et al., Effects of NZ–107 on Airway Inflammation and Cell Activation in Guinea Pigs, Apr., 1993.

Vanden Boesche et al., Br. J. Clin. Pract. Symp. Suppl., (1990 Sep.) 71, pp. 41–46, Abstract.

*Primary Examiner*—Phyllis G. Spivack
*Attorney, Agent, or Firm*—Waddey & Patterson; Mark J. Patterson

[57] ABSTRACT

This invention relates to a method for the inhibition of the metabolic activity of cytochrome P450 enzymes by topical administration of a cytochrome P450 inhibitor. Particularly, this invention relates to a method for inhibition of the metabolic activity of cytochrome P450 in the lungs or nasal membranes of a patient by topical administration of a cytochrome P450 inhibitor by inhalation. The effect of the inhibition of cytochrome P450 activity is the increase in the localized concentration of administered or endogenous steroids normally metabolized by the cytochrome P450. This increased concentration of steroid results in the more effective treatment of inflammatory conditions of the lungs and nasal membranes.

30 Claims, No Drawings

METHOD FOR TOPICAL INHIBITION OF THE METABOLIC ACTIVITY OF CYTOCHROME P450

GRANT STATEMENT

This research was supported in part by the National Institute of Health, Grant GM07569-15 and the Government has certain fights in the invention.

BACKGROUND OF THE INVENTION

The present invention relates generally to the topical inhibition of the metabolic activity of cytochrome P450 and more specifically to the topical administration of cytochrome P450 inhibitors to facilitate localized inhibition of the metabolic activity of different enzymes within the cytochrome P450 family.

It will be appreciated by those skilled in the art that topical steroids are currently the drugs of choice for the treatment of moderate and severe asthma. Though topical steroids are generally well tolerated and have less side effects than systemic steroids, the possibility of side effects, including osteoporosis, impeded linear growth in children and cataract formation, is still a concern.

Corticosteroids have been used to treat asthma since 1950. These drugs do not relax smooth muscle in the airway directly. It has been suggested by studies that corticosteroids may act by up-regulating β-receptors as well as by inhibiting the inflammatory response in the airways. Because of severe adverse effects when oral corticosteroids are given chronically, oral steroids are generally reserved for patients who are not maintained adequately with bronchodilators or for acute treatment in patients with worsening symptoms despite bronchodilator therapy.

The introduction of inhaled corticosteroids was, therefore, a great therapeutic advance. By introducing lipid soluble corticosteroids in aerosol form, an effective method of delivering corticosteroids to the airways with minimal systemic absorption and reduced adverse effects was established.

There have also been attempts to develop a more effective inhalation method for the treatment of asthma. One such attempt was disclosed in U.S. Pat. No. 4,089,959, issued to J. Diamond on May 16, 1978 which describes a long-acting xanthine bronchodilator. This long-acting xanthine was an attempt of an improvement over previously developed substituted xanthines and the well known theophylline (1-3-dimethylxanthine). None of the compounds used in the present invention are related to the family of substituted xanthines described in the '959 patent.

Another such attempt was made in U.S. Pat. No. 5,081,114, issued to J. Gourvest, et al on Jan. 14, 1992 which disclosed novel steroid compounds. Use of these steroids is unrelated to the present invention. These steroids are capable of inducing aromatase specific activity (cytochrome P450 aromatase) in warm-blooded animals. The use of aromatase specific activity induction is found useful in the treatment of cancer of the breast, endometrium, ovary, pancreas and etc. However, no mention is made of treatment of asthma by using this compound and no mention is made of topical inhibition of cytochrome P450 enzymes.

U.S. Pat. No. 5,215,965, issued to J. Lezdey, et al on Jun. 1, 1993, describes a treatment for inflammation by administering a corticosteroid in combination with at least one serine protease inhibitor, its salts, derivatives or analogs which bind the mediators of mast cells or T-cells. The '965 invention addresses the fact that in certain pulmonary diseases, neutrophils, mast cells, T-cells, and their mediators induced an inflammatory state resulting in a localized imbalance of elevated serine protease with an accompanying reduction in their naturally occurring inhibitors. Although this combination of compounds is via inhalatory route, it differs greatly from the combination suggested in the proposed invention.

In the article by Mary Ann Christopher, et al. entitled *Clinical Relevance of the Interaction of Theophylline with Diltiazem or Nifedipine* published in Chest, February, 1989; 95(2): 309–313, the authors demonstrated that although calcium channel blockers are capable of inhibiting cytochrome P-450 activity in hepatic microsomes (the pathway of theophylline metabolism), the actual metabolism of theophylline was not effected by administration of certain administered calcium channel blockers. This study, although it deals with P-450 activity and compounds which inhibit the same activity, is unrelated to the present invention.

*The Effects of Imidazole Derivatives on Cytochrome P-450 From Human Hepatocytes in Primary Culture*, FASEB J 1992; 6:752–58 by Manuelle Mattrice, et al., reported on in vitro tests on human hepatocytes which examined the effects of imidazole derivatives on cytochrome P-450. Ketoconazole was found to be a strong and selective inhibitor of P-450 3A (cyclosporin oxidase or CYP 3A). However, an application of that inhibition was not further discussed in the paper nor suggested.

Cytochrome P-450 is a superfamily of enzymes that metabolize a large number of drugs, xenobiotics and endogenous substances in vitro and in vivo. The cytochrome P-450 3A (CYP 3A) isoenzyme is a member of the cytochrome P-450 superfamily. It constitutes up to 60% of the total human liver microsomal cytochrome P-450 and is responsible for metabolism of a large number of drugs including nifedipine, macrofide antibiotics including erythromycin and troleandomycin, cyclosporin, FK506, teffenadine, tamoxifen, lidocaine, midazolam, triazolam, dapsone, diltiazem, lovastatin, quinidine, ethylestradiol, testosterone, and alfentanil.

Metabolism of cortisol to 6-b-hydroxycortisol has also been shown to be specifically mediated by cytochrome P450 in vitro and in vivo. In addition, CYP 3A has been shown to be involved in both bioactivation and detoxication pathways for several carcinogens in vitro. (Bibliography refs. 1 and 2)

The active form of CYP 3A has been found in other organs besides the liver including kidney epithelial cells, jejunal mucosa, and the lungs. In these organs, the amount of the cytochrome P450 protein is much lower then in the liver. In a study of human lung microsomes, presence and activity of CYP 3A has been demonstrated. (Bibliography ref. 3)

Presence of the cytochrome P-450 3A in the lung microsomes indicates that the drugs and other substances which are subject to CYP 3A (P450-3A) mediated metabolism may be partially metabolized in the lungs. This has been demonstrated for the topical steroid, beclomethasome dipropionate. It has also been shown that only about 10% of the drug released by an inhaler is available to the lungs. The remaining mount is retained in the spacer device and oral cavity. Steroids absorbed from the lungs and gastrointestinal tract are subsequently metabolized by hepatic cytochrome P450. (Bibliography ref. 4)

The ideal topical steroid for asthma therapy should have very high topical activity, and be poorly absorbed from the lungs and GI tract with the absorbed portion of the dose quickly metabolized by the liver enzymes.

SUMMARY OF THE INVENTION

It is an object of this invention to provide a method of topical inhibition of cytochrome P450 in the lungs and nasal passages.

It is another object of this invention to provide a method of treating inflammatory conditions of the lungs and nasal membranes by topical administration of a cytochrome P450 inhibitor.

A further object of this invention is to provide a method for treating asthma and other inflammatory respiratory conditions by administering a cytochrome P450 enzyme inhibitor in conjunction with inhaled anti-inflammatory agents, e.g. corticosteroids, cyclosporin, etc.

It is also an object of this invention to use topical inhibitors of cytochrome P450 alone to slow the topical metabolism of endogenous steroids in the target organ(s).

Another object of this invention to provide a method for treating asthma and other inflammatory respiratory conditions which will allow for a lower systemic dose of corticosteroids, i.e. be steroid sparing, and thereby reduce steroid side effects. According to this invention, prolonged bronchodilation and prolonged inhibition of inflammatory mediator release are produced by administering an effective amount of a corticosteroid known to be useful in the treatment of asthma in conjunction with an inhibitor of the cytochrome P-450 enzyme metabolizing that corticosteroid. A known example of an inhibitor of that enzyme is ketoconazole.

DESCRIPTION OF THE PREFERRED EMBODIMENT

Cytochrome P450 inhibitors may be used topically to inhibit the metabolism of endogenous steroids and topical antiflammatory agents including corticosteroids used for the treatment of inflammatory conditions of the lungs and nasal membranes. These conditions include but are not limited to bronchial asthma and allergic rhinitis. The cytochrome P450 inhibitors may also be used topically to inhibit metabolism of immunosuppressive drugs (e.g. cyclosporin) in the lungs and intestine in organ transplant patients. Thus, the cytochrome P450 inhibitors may be given in combination with other drugs (such as topical steroids or immunosuppressants), or alone.

Topical inhibition of cytochrome P450 enzymes in the lungs and nasal mucosa can be accomplished by inhalation of cytochrome P450 inhibitors, which could include: ketoconazole and other imidazole antifungals, troleandomycin, erythromycin, nifedipine and other calcium channel blockers, or gestodene. Another known potent inhibitor of cytochrome P450 3A (CYP3A) is naringenin, found in grapefruit.

Troleandomycin (Triacetyloleandomycin, TAO) is a macrofide antibiotic. It has been previously used for the treatment of respiratory tract infections. Troleandomycin is rapidly hydrolyzed in the liver to the more active oleandomycin. Troleandomycin has been used in the treatment of bronchial asthma as orally administered capsules. It has been shown that troleandomycin reduces the clearance of methylprednisolone and theophylline in asthmatic subjects. The use of troleandomycin allowed reduction of the oral methylprednisolone dose by 50%. (Bibliography ref. 5) The use of troleandomycin has also been reported in steroid-dependent asthma without concomitant administration of corticosteroids. (Bibliography ref. 7) It has also been suggested that macrolide antibiotics and imidazole antifungals possess intrinsic anti-inflammatory properties. (Bibliography ref. 7)

Troleandomycin used in oral form has been reported to cause multiple drug interactions as well as various side effects including cholestatic jaundice. These in part limit more active use of troleandomycin in bronchial asthma.

No drug is currently used for the specific purpose of topical inhibition of the cytochrome P450 activity. Among currently used drugs that inhibit Cytochrome P450 3A, ketoconazole is the most potent. Ketoconazole is a synthetic broad-spectrum antifungal agent. It has been shown to alter the metabolism of steroids, specifically testosterone and methylprednisolone. (Bibliography ref. 8) At conventional doses (200–400 mg po), it appears to be well tolerated in most patients. Many other antibiotics including carbenicillin, aminoglycosides, and even amphotericin B have been previously aerosolized with minimal or no side effects.

According to the present invention, the metabolic activity of cytochrome P450 is inhibited by topical administration of a known cytochrome P450 inhibitor. In the preferred embodiment of the method, an inhaled form of ketoconazole is used in combination with an inhaled steroid for the treatment of asthma. Ketoconazole can be administered in powdered form via a hand held, breath actuated device (e.g. Rotohaler, Allen and Hanburys). Topical inhibition of the cytochrome P-450 metabolic activity in the lungs is accomplished by administration of aerosolized ketoconazole in a dose of 10 mg once or twice daily. An example of an inhaled steroid is the corticosteroid, beclomethasone. Decreased local metabolism of administered and endogenous steroids in the lungs occurs, resulting in relatively increased local steroid concentration in the lungs compared to the uninhibited state. This increased concentration of steroids enhances anti-inflammatory effects leading to a decrease in non-specific hyperactivity of the airways as reflected by the methacholine bronchoprovocation test, a test known to measure the degree of reactivity along the airways. The hepatic metabolism of the steroids should not be effected to a noticeable extent because the inhibitor is used in a dose insufficient to inhibit a significant amount of hepatic Cytochrome P450.

The dosage range is determined based on known potency of ketoconazole as a CYP3A inhibitor and milligram comparison of inhaled steroid/oral steroid equivalency in terms of their effects on the inflammation along the airways. By that comparison, a 20–40 fold lower than the usual oral dose of ketoconazole is given via inhalation.

The treatment of inflammatory conditions of the nasal membranes is accomplished in a method similar to the preferred embodiment.

After an organ transplant procedure, a cytochrome P450 inhibitor administered topically and concomitantly with administration of an immunosuppressant drug increases the effectiveness of the drug. An example of an immunosuppressant drug is cyclosporin, which acts by suppressing inflammatory responses produced by the immune system. Topical inhibition of the cytochrome P-450 metabolic activity in the lungs, for example, results in decreased metabolism of administered immunosuppressant drug in the lungs. This inhibition results in relatively increased drug concentration in the target organ compared to the uninhibited state. This increased concentration of the drug enhances the local suppression of the immune system, improving the chance of transplantation success.

Using ketoconazole as an example, the dosage range is determined based on known potency of ketoconazole as a CYP3A inhibitor and milligram comparison of inhaled steroid/oral steroid equivalency in terms of their effects on the inflammation along the airways. By that comparison, a 20–40 fold lower than the usual oral dose of ketoconazole is given via inhalation.

Thus, although particular embodiments of the present invention of a new and useful method for topical inhibition of the metabolic activity of cytochrome P450 have been described, it is not intended that such references be construed as limitations upon the scope of this invention except as set forth in the following claims. Similarly, although certain dose and other parameters in the preferred embodiment have been elucidated, it is not intended that such be construed as limitations upon the scope of this invention except as set forth in the following claims.

We claim:

1. A method for inhibiting catabolic activity of cytochrome P450 in a patient by topical administration of a cytochrome P450 inhibitor wherein the cytochrome P450 inhibitor comprises an imidiazole antifugal.

2. The method described in claim 1 where the cytochrome P450 catabolic activity is the catabolism of steroids in the lungs of a patient.

3. The method described in claim 1 where the cytochrome P450 catabolic activity is the catabolism of steroids in the nasal membranes of a patient.

4. The method described in claim 1 where the cytochrome P450 catabolic activity is the catabolism of immunosuppressive drugs in a patient.

5. The method described in claim 4 wherein the immunosuppressive drug comprises cyclosporin.

6. A method of treatment of inflammatory conditions of a patient's lungs comprising the topical administration of a cytochrome P450 inhibitor by inhalation, where the inhibitor comprises an imidiazole antifungal.

7. The method described in claim 6 where the imidazole antifungal comprises ketoconazole.

8. The method described in claim 7 where the ketoconazole is administered by inhaler in a dose in the range 5 to 20 mg once or twice daily.

9. The method described in claim 6 where the imidazole antifungal comprises miconazole.

10. A method for treatment of inflammatory conditions of a patient's lungs comprising topical administration of asteroid and administration of a cytochrome P450 inhibitor by inhalation, where the inhibitor comprises an imidazole antifungal.

11. The method described in claim 10 where the imidazole antifungal comprises ketoconazole.

12. The method described in claim 11 where the ketoconazole is administered by inhaler in a dose in the range 5 to 20 mg once or twice daily.

13. The method described in claim 10 where the imidazole antifungal comprises miconazole.

14. The method described in claim 10 where the steroid comprises a corticosteroid.

15. The method described in claim 14 where the corticosteroid comprises beclomethasone.

16. A method for treatment of inflammatory conditions of a patient's nasal membranes comprising topical administration of a cytochrome P450 inhibitor by inhalation where the inhibitor comprises an imidazole antifungal.

17. The method described in claim 16 where the imidazole antifungal comprises ketoconazole.

18. The method described in claim 17 where the ketoconazole is administered by inhaler in a dose in the range 5 to 20 mg once or twice daily.

19. The method described in claim 16 where the imidazole antifungal comprises miconazole.

20. A method of improving the effectiveness of a steroid which is administered topically in the treatment of inflammatory conditions in a patient's lungs, the method comprising administering by inhalation an agent for inhibiting cytochrome P450 in an amount sufficient to inhibit metabolism of the steroid in the lungs or nose of the patient being treated with the steroid, where the inhibitor comprises an imidazole antifungal.

21. The method described in claim 20 where the imidazole antifungal comprises ketoconazole.

22. The method described in claim 21 where the ketoconazole is administered by inhaler in a dose in the range 5 to 20 mg once or twice daily.

23. The method described in claim 20 where the imidazole antifungal comprises miconazole.

24. The method described in claim 20 in which the steroid comprises a corticosteroid.

25. The method described in claim 24 where the corticosteroid comprises beclomethasone.

26. A method of improving the effectiveness of asteroid endogenous to the lungs of a patient in the treatment of inflammatory conditions of the patient's lungs, the method comprising administering by inhalation an agent for inhibiting cytochrome P450 in an amount sufficient to inhibit metabolism of the steroid in the lungs of the patient, where the inhibitor comprises an imidazole antifungal.

27. The method described in claim 26 where the imidazole antifungal comprises ketoconazole.

28. The method described in claim 27 where the ketoconazole is administered by inhaler in a dose in the range 5 to 20 mg once or twice daily.

29. The method described in claim 26 where the imidazole antifungal comprises miconazole.

30. A therapeutic composition for topical treatment of inflammatory conditions in a patient, the composition comprising a steroid and a cytochrome P450 inhibitor, the steroid and the inhibitor each adapted for topical administration to the patient by inhalation, where the inhibitor comprises an imidazole antifungal.

* * * * *

UNITED STATES PATENT AND TRADEMARK OFFICE
CERTIFICATE OF CORRECTION

PATENT NO. : 5,658,881
DATED : Aug. 19, 1997
INVENTOR(S) : Gelland, et. al.

It is certified that error appears in the above-identified patent and that said Letters Patent is hereby corrected as shown below:

Column 1, lines 7-9 should read as follows:

" This research was supported in part by the National Institute of Health, Grant GM07569-15 and the Government has certain rights in the invention."

Signed and Sealed this

Twenty-third Day of March, 1999

Attest:

Q. TODD DICKINSON

Attesting Officer     Acting Commissioner of Patents and Trademarks